United States Patent
Guo et al.

(10) Patent No.: US 11,287,356 B1
(45) Date of Patent: Mar. 29, 2022

(54) VARIABLE ANGLE LOADING TESTING MACHINE

(71) Applicant: INSTITUTE OF GEOLOGY AND GEOPHYSICS, Beijing (CN)

(72) Inventors: Songfeng Guo, Beijing (CN); Shengwen Qi, Beijing (CN); Ming Cai, Ontario (CA); Yanjun Shang, Beijing (CN); Qingze Hao, Changchun (CN); Haijun Zhao, Beijing (CN); Zhendong Cui, Beijing (CN); Lei Xue, Beijing (CN); Xueliang Wang, Beijing (CN); Zhaobin Zhang, Beijing (CN); Xiaolin Huang, Beijing (CN); Ning Liang, Beijing (CN); Bowen Zheng, Beijing (CN); Yu Zou, Beijing (CN); Xin Wang, Jilin (CN); Xiaokun Hou, Beijing (CN); Shuaihua Song, Beijing (CN); Feng Xiong, Beijing (CN); Yongchao Li, Beijing (CN); Lina Ma, Beijing (CN); Fengjiao Tang, Beijing (CN); Xin Wang, Jilin (CN); Libo Jiang, Jilin (CN); Jinxuan Li, Beijing (CN); Yidong Xiao, Beijing (CN)

(73) Assignee: INSTITUTE OF GEOLOGY AND GEOPHYSICS, Beijing (CN)

( * ) Notice: Subject to any disclaimer, the term of this patent is extended or adjusted under 35 U.S.C. 154(b) by 0 days.

(21) Appl. No.: 17/474,204

(22) Filed: Sep. 14, 2021

(30) Foreign Application Priority Data

Jul. 19, 2021 (CN) .......................... 202110813429.2

(51) Int. Cl.
*G01N 3/04* (2006.01)
*G01N 3/08* (2006.01)

(52) U.S. Cl.
CPC ................. *G01N 3/04* (2013.01); *G01N 3/08* (2013.01); *G01N 2203/0017* (2013.01); *G01N 2203/04* (2013.01)

(58) Field of Classification Search
CPC .... G01N 3/04; G01N 3/08; G01N 2203/0017; G01N 2203/04
See application file for complete search history.

(56) References Cited

U.S. PATENT DOCUMENTS

| | | | | |
|---|---|---|---|---|
| 2012/0198942 | A1* | 8/2012 | Zampieri | ................. G01N 3/20 73/849 |
| 2014/0053655 | A1* | 2/2014 | McMullen | ............... A61C 8/00 73/821 |

FOREIGN PATENT DOCUMENTS

| | | |
|---|---|---|
| CN | 207051095 U | 2/2018 |
| CN | 112903463 A | 6/2021 |

OTHER PUBLICATIONS

R. S. Read, N. A. Chandler, E. J. Dzik, "In Situ Strength Criteria for Tunnel Design in Highly-stressed Rock Masses", Int. J. Rock Mech. Min. Sci. vol. 35, No. 3, pp. 261-278, 1998.

(Continued)

*Primary Examiner* — Jonathan M Dunlap
(74) *Attorney, Agent, or Firm* — WPAT, PC

(57) ABSTRACT

A variable angle loading testing machine is provided, which may include a bottom plate and a base fixedly connected to the bottom plate. A rock-sample accommodating cavity is formed in the base, and a rectangle-shaped sample is suitable for being placed into the rock-sample accommodating cavity. A side of the base is fixedly connected to two arc-shaped tension beams arranged in parallel, and a variable angle loading mechanism is slidably connected between the two arc-shaped tension beams. Through-holes are formed on the base, and an output end of the variable angle loading mechanism abuts against the rectangle-shaped sample (Continued)

through one of the through-holes. Loading and unloading of a stress with variable direction and magnitude under excavation disturbance can be simulated, which is of great significance for understanding mechanical behaviors of rock-soil mass under excavation disturbance.

10 Claims, 5 Drawing Sheets

(56) References Cited

OTHER PUBLICATIONS

E. Eberhardt, "Numerical modelling of three-dimension stress rotation ahead of an advancing tunnel face", International Journal of Rock Mechanics & Mining Sciences 38(2001) pp. 499-518.
M. Cai, P. K. Kaiser, "In-situ Rock Spalling Strength near Excavation Boundaries", Rock Mech Rock Eng, May 25, 2013.
Songfneg Guo, Shengwen Qi, Ming Cai, "Influence of tunnel wall roughness and localized stress concentrations on the initiation of brittle spalling", Bull Eng Geol Environ (2016) 75:1597-1607.
China National Intellectual Property Administration, Office Action dated Dec. 3, 2021.

* cited by examiner

VARIABLE ANGLE LOADING TESTING MACHINE

FIELD OF THE DISCLOSURE

The disclosure relates to the field of rock testing technologies, and more particularly to a variable angle loading testing machine.

BACKGROUND OF THE DISCLOSURE

Previous studies have shown that magnitude and direction of a force on the rock-soil mass in front of the tunnel face are changing under excavation disturbance (Read et al., "In Situ Strength Criteria for Tunnel Design in Highly-stressed Rock Masses", Int. J. Rock Mech. Min. Sci. Vol. 35, No. 3, pp. 261-278, 1998; and Eberhardt, "Numerical modelling of three-dimension stress rotation ahead of an advancing tunnel face", International Journal of Rock Mechanics & Mining Sciences 38(2001) pp. 499-518). In the process of tunnel excavation, the stress values and magnitudes at different positions of the tunnel change continuously with the advance of the tunnel face. It makes the force direction of rock-soil mass always change in practical engineering, and the crack initiation, propagation and evolution in rock-soil mass become more complex under the action of the variable loading direction force. At present, adopting uniaxial or triaxial loading to obtain the deformation and strength characteristics of rock mass in the laboratory, the loading is simply loading along a fixed direction (axial) until the sample is damaged, and the stress path is completely different from the stress path of engineering rock mass. Therefore, the crack initiation and propagation stress and peak strength obtained in the laboratory are very different from the crack initiation and propagation stress and strength of rock mass at a construction site, so it is difficult to effectively predict the strength of engineering rock mass (Cai and Kaiser, "In-situ Rock Spalling Strength near Excavation Boundaries", Rock Mech Rock Eng, 25 May 2013; and Guo et al., "Influence of tunnel wall roughness and localized stress concentrations on the initiation of brittle Spalling", Bull Eng Geol Environ (2016) 75:1597-1607).

SUMMARY OF THE DISCLOSURE

An objective of the disclosure is to provide a variable angle loading testing machine to thereby solve the problems existing in the prior art.

In order to achieve the above-mentioned objective, solutions are provided as follows. The disclosure provides a variable angle loading testing machine, which may include a bottom plate and a base fixedly connected to the bottom plate. A rock-sample accommodating cavity is formed in the base, and the rock-sample accommodating cavity is configured to be placed a rectangle-shaped sample therein. A side of the base is fixedly connected to two arc-shaped tension beams arranged in parallel, a variable angle loading mechanism is slidably connected between the two arc-shaped tension beams. through-holes are formed on the base, and an output end of the variable angle loading mechanism is configured to abut against the rectangle-shaped sample through one of the through-holes.

In an embodiment of the disclosure, the variable angle loading mechanism may include a first pressure cylinder slidably connected between the two arc-shaped tension beams, and an output end of the first pressure cylinder is fixedly connected with a pressure pad. A side of the pressure pad away from the first pressure cylinder is fixedly connected to a side of a load sensor, another side of the load sensor is fixedly connected to a round indenter, and the round indenter is configured to abut against the rectangle-shaped sample. Piston cylinders are symmetrically hinged on the first pressure cylinder, each of the piston cylinders is located between the two arc-shaped tension beams, and each of the piston cylinders is hinged to the arc-shaped tension beam.

In an embodiment of the disclosure, a first pressure plate and multiple second pressure plates are configured to be fixedly connected to an outside of the rectangle-shaped sample, the multiple second pressure plates abut against the rock-sample accommodating cavity, a side of the first pressure plate away from the rectangle-shaped sample is provided with an arc-shaped groove matched with the round indenter, and the round indenter abuts against the arc-shaped groove.

In an embodiment of the disclosure, a side of the first pressure cylinder away from the pressure pad is fixedly connected to two pulling plates, a side of the first pressure cylinder close to the pressure pad is fixedly connected to supporting plates, and the two arc-shaped tension beams are located between the supporting plates and the two pulling plates. Ends of the two pulling plate and the supporting plates are rotatably connected with rollers, and the rollers are slidably engaged with the arc-shaped tension beam.

In an embodiment of the disclosure, the through-hole may include a first through-hole, a second through-hole, a fourth through-hole, a fifth through-hole and a sixth through-hole. The second through-hole, the fourth through-hole, the fifth through-hole and the sixth through-hole are located in a same plane, and axes of the second through-hole, the fourth through-hole, the fifth through-hole and the sixth through-hole are all perpendicular to an axis of the first through-hole. The directional loading mechanisms are respectively arranged in the second through-hole, the fourth through-hole, the fifth through-hole and the sixth through-hole; and the directional loading mechanism arranged in the sixth through-hole is fixedly connected to the bottom plate. Output ends of the directional loading mechanisms abut against the second pressure plates. The variable angle loading mechanism abuts against the first pressure plate through the first through-hole.

In an embodiment of the disclosure, each of the directional loading mechanisms may include a second pressure cylinder, a piston end of the second pressure cylinder is fixedly connected to a second pressure pad. A side of the second pressure pad away from the second pressure cylinder is fixedly connected to a second load sensor, another side of the second load sensor is fixedly connected to a ball seat, an end of the ball seat away from the second load sensor is fixedly connected to a joint, and the joint abuts against the second pressure plate.

In an embodiment of the disclosure, a third through-hole is formed on a side of the base away from the first through-hole, the third through-hole is coaxial with the first through-hole, and the third through-hole is communicated with the rock-sample accommodating cavity. The bottom plate is fixedly connected to supporting pillars, an end of each of the supporting pillars away from the bottom plate is fixedly connected to a lower beam, a side of the base away from the arc-shaped tension beams is fixedly connected to columns, and an end of each of the columns away from the base is fixedly connected to the lower beam. The lower beam is provided with a mounting hole, the directional loading mechanism is installed in the mounting hole, and the output end thereof abuts against the second pressure plate through the third through-hole.

In an embodiment of the disclosure, each of the first pressure cylinder and the second pressure cylinders is mounted a displacement sensor thereon.

In an embodiment of the disclosure, rotating sleeves is arranged between the two arc-shaped tension beams, the rotating sleeves are rotatably connected to the two arc-shaped tension beams, and the piston cylinders are rotatably connected to two arc-shaped tension beams through the rotating sleeves respectively.

In an embodiment of the disclosure, both sides of the first pressure cylinder are fixedly connected to articulated bases respectively, and output ends of the piston cylinders are hinged with the first pressure cylinder through the articulated bases respectively.

Compared with the related art, the embodiments of the disclosure may mainly have the following beneficial effects.

The disclosure discloses a multi-directional loading testing device, which can simulate loading and unloading of a stress with changing direction and magnitude under excavation disturbance, and is of great significance for understanding the mechanical behavior of rock-soil mass under excavation disturbance.

BRIEF DESCRIPTION OF THE DRAWINGS

In order to more clearly explain technical solutions of embodiments of the disclosure or the prior art, drawings used in the embodiments will be briefly introduced below. Apparently, the drawings described below are only some embodiments of the disclosure. For those skilled in the art, other drawings can be obtained from these illustrated drawings without paying any creative effort.

Figure 1:
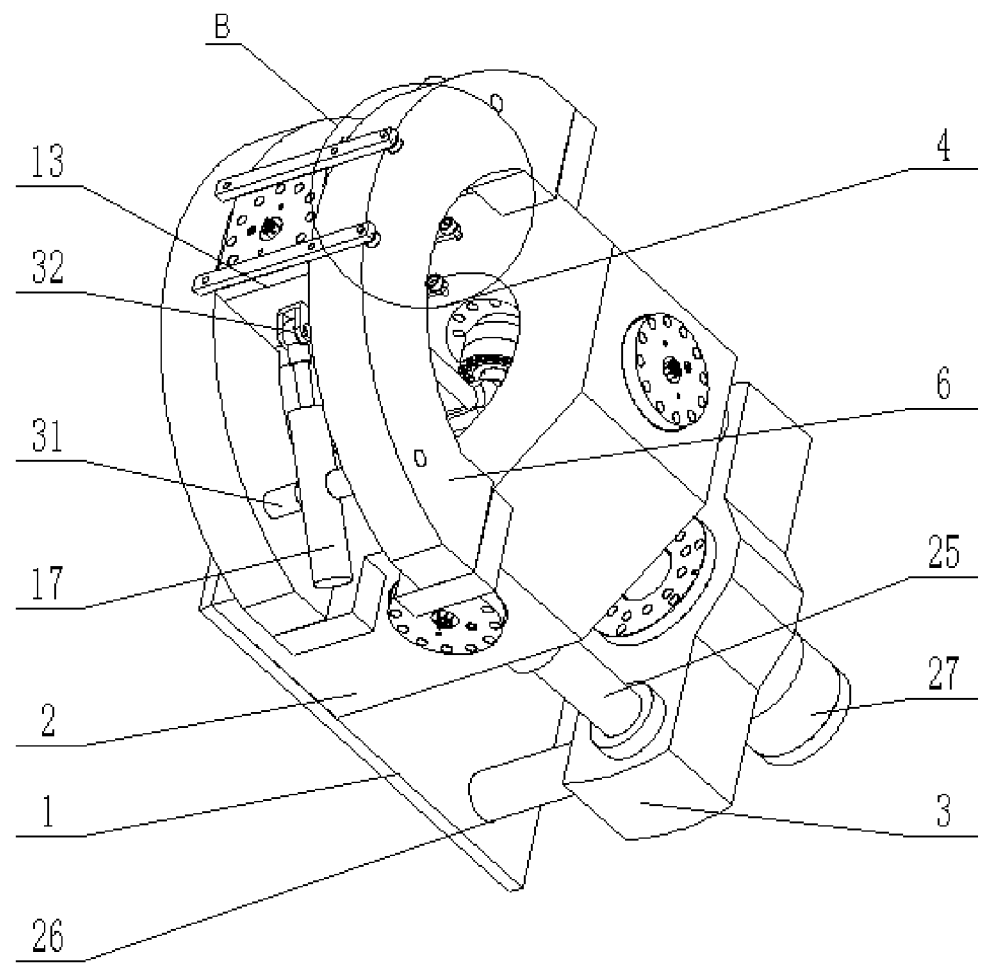
FIG. 1 is a schematic axonometric view of a variable angle loading testing machine of the disclosure.
Figure 2:
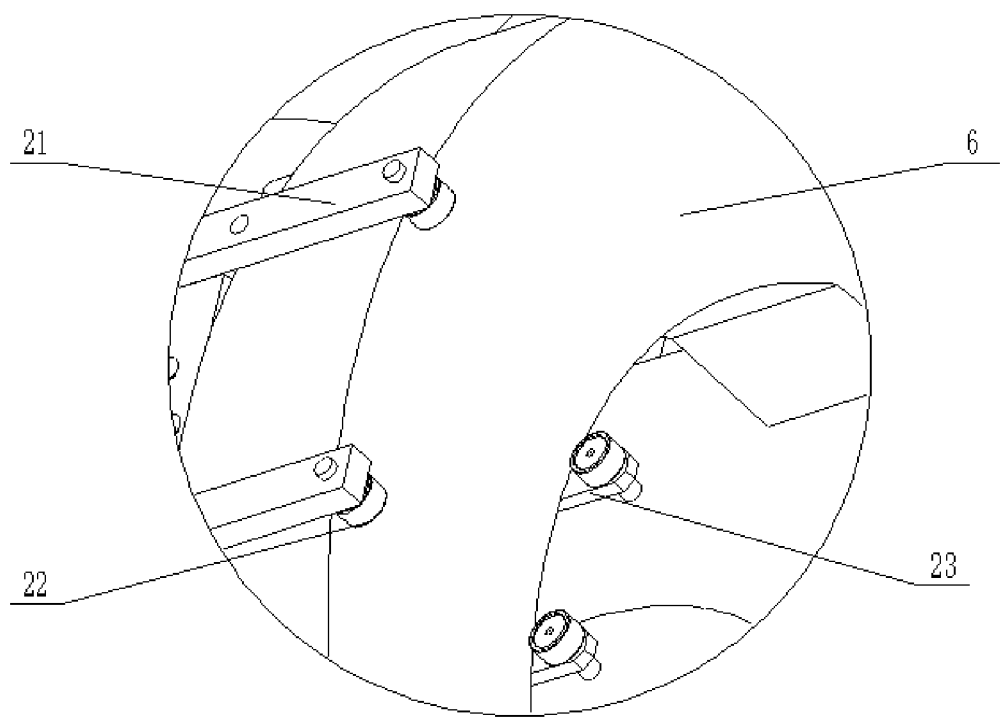
FIG. 2 is a schematic enlarged view of the portion B in FIG. 1.
Figure 3:
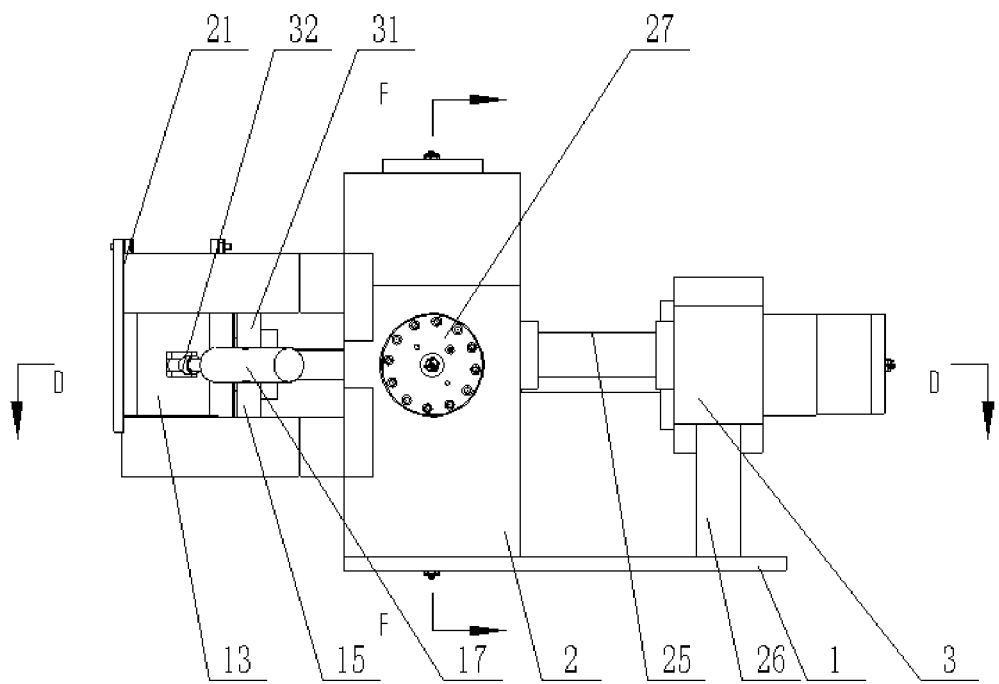
FIG. 3 is a front view of the variable angle loading testing machine of the disclosure.
Figure 4:
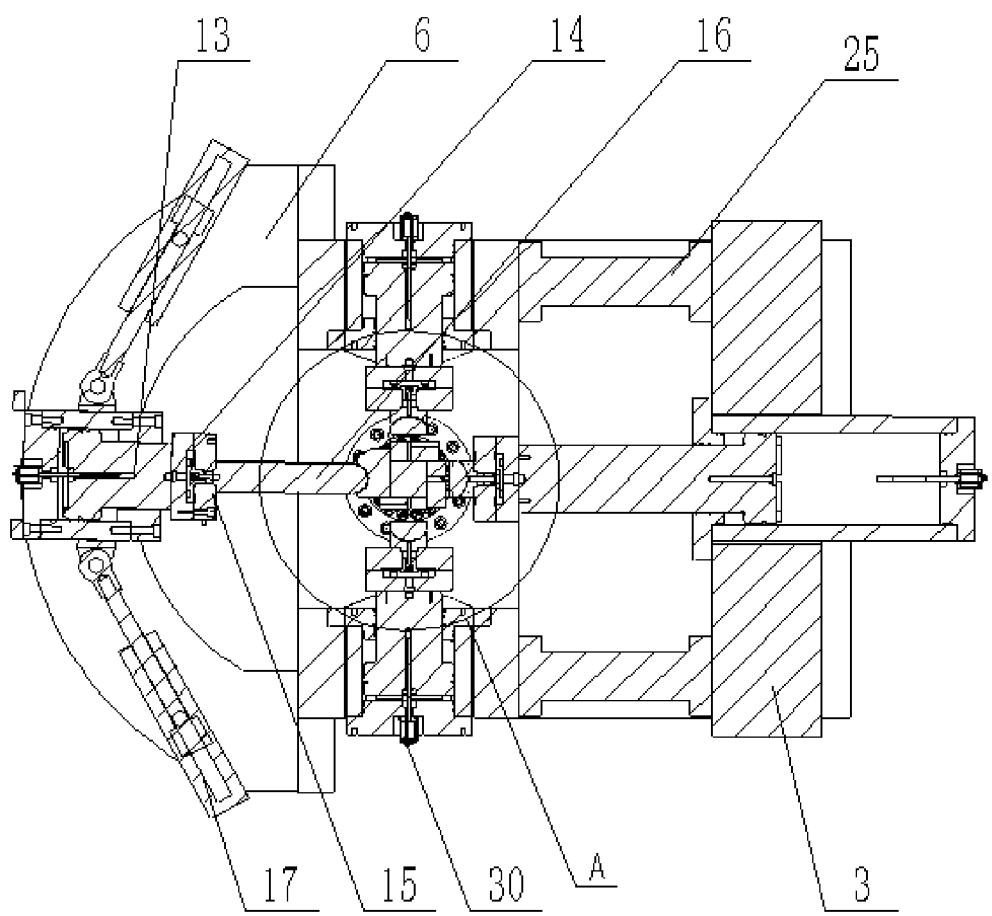
FIG. 4 is a schematic cross-sectional view taken along D-D direction in FIG. 3.
Figure 5:
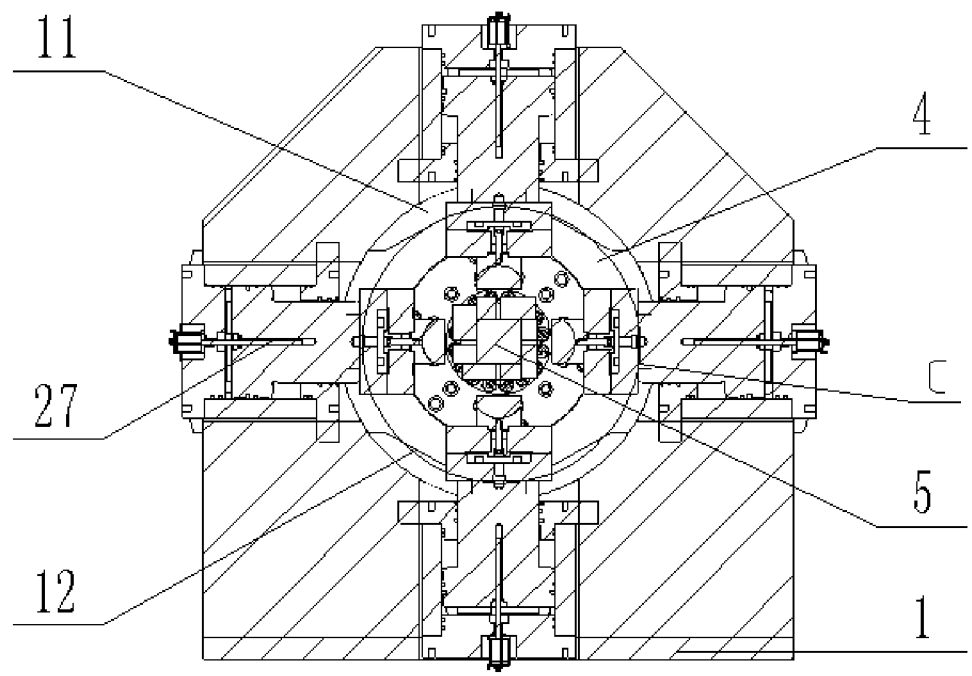
FIG. 5 is a schematic cross-sectional view taken along F-F direction in FIG. 3.
Figure 6:
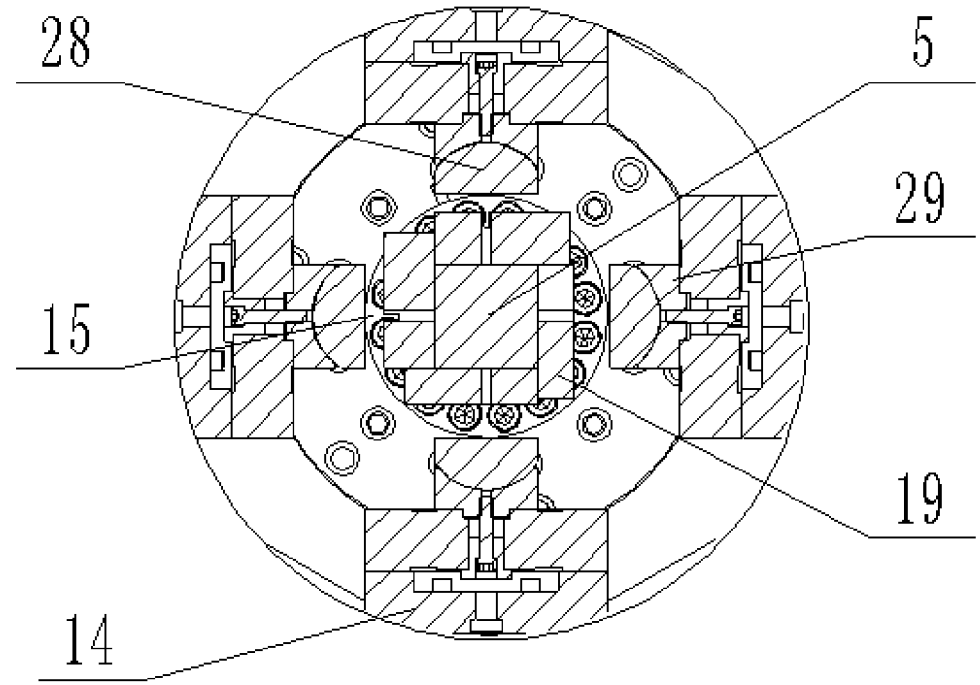
FIG. 6 is a schematic enlarged view of the portion C in FIG. 5.
Figure 7:
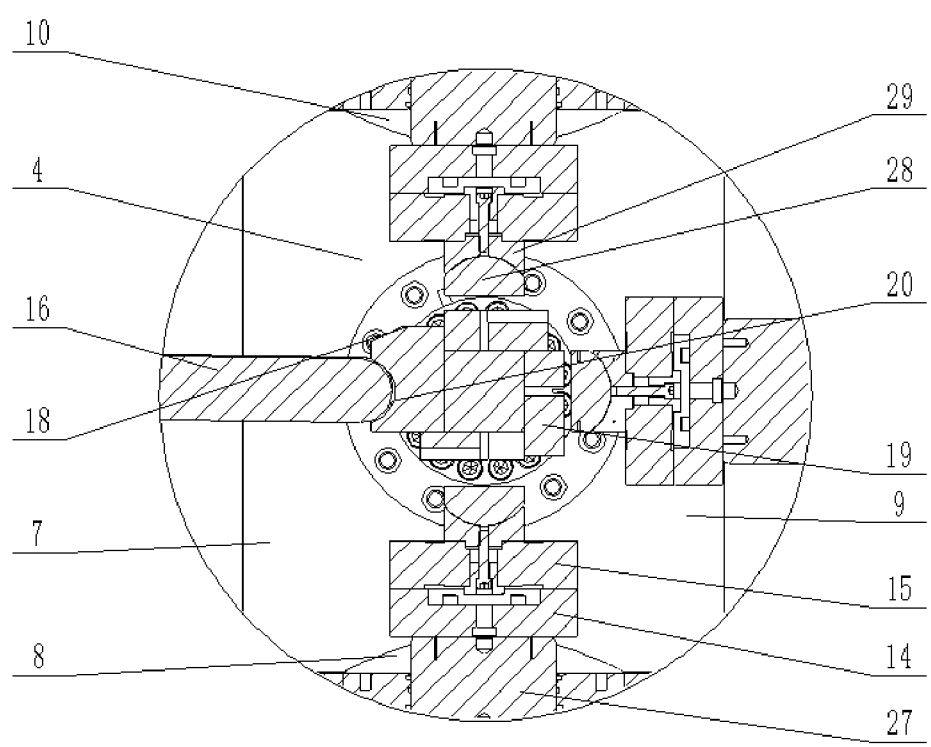
FIG. 7 is a schematic enlarged view of the portion A in FIG. 4.

Description of reference numerals: bottom plate—1, base—2, lower beam—3, rock—sample accommodating cavity—4, rectangle-shaped sample—5, arc-shaped tension beam—6, first through-hole—7, second through-hole—8, third through-hole—9, fourth through-hole—10, fifth through-hole—11, sixth through-hole—12, first pressure cylinder—13, pressure pad—14, load sensor—15, round indenter—16, piston cylinder—17, first pressure plate—18, second pressure plate—19, arc-shaped groove—20, pulling plate—21, roller—22, supporting plate—23, column—25, supporting pillar—26, second pressure cylinder—27, joint—28, ball seat—29, displacement sensor—30, rotating sleeve—31, articulated base—32.

DETAILED DESCRIPTION OF EMBODIMENTS

Technical solutions of embodiments of the disclosure will be clearly and completely described below with reference to the accompanying drawings of the embodiments of the disclosure. Apparently, the described embodiments are only part of embodiments of the disclosure, not all of embodiments of the disclosure. Based on the illustrated embodiments of the disclosure, all other embodiments obtained by those skilled in the art without creative work/effort belong to the protection scope of the disclosure.

In order to make the above-mentioned objectives, features and advantages of the disclosure more obvious and understandable, the disclosure will be described in further detail below in combination with the accompanying drawings and specific embodiments.

The disclosure provides a variable angle loading testing machine, which may include a bottom plate 1 and a base 2 fixedly connected to the bottom plate 1. A rock-sample accommodating cavity 4 is formed in the base 2, and the rock-sample accommodating cavity 4 is configured to be placed a rectangle-shaped sample 5 therein. A side of the base 2 is fixedly connected to two arc-shaped tension beams 6 arranged in parallel, and a variable angle loading mechanism is slidably connected between the two arc-shaped tension beams 6. Through-holes are formed on the base 2, and an output end of the variable angle loading mechanism is configured to abut against the rectangle-shaped sample 5 through one of the through-holes.

Further, in order to ensure that the machine can load the rectangle-shaped sample 5 in a tower-type vessel (i.e., sample accommodating cavity) in all directions, a first through-hole 7, a second through-hole 8, a third through-hole 9 and a fourth through-hole 10 are formed on the base 2 at equal intervals in a horizontal circumferential direction, and a fifth through-hole 11 and a sixth through-hole 12 coaxially arranged are formed on the base 2 in a vertical direction. The first through-hole 7, the second through-hole 8, the third through-hole 9, the fourth through-hole 10, the fifth through-hole 11 and the sixth through-hole 12 are communicated with the rock-sample accommodating cavity 4. The first through-hole 7 and the third through-hole 9 are arranged coaxially, and the second through-hole 8 and the fourth through-hole 10 are arranged coaxially. An intersection of the axes of the first through-hole 7, the second through-hole 8 and the fifth through-hole 11 is located in a center of the rock-sample accommodating cavity 4. Directional loading mechanisms are respectively arranged in the second through-hole 8, the third through-hole 9, the fourth through-hole 10, the fifth through-hole 11 and the sixth through-hole 12, and an output end of the variable angle loading mechanism extends into the rock-sample accommodating cavity 4 through the first through-hole 7 and abuts against the rectangle-shaped sample 5. By controlling the directional loading mechanism in the second through-hole 8 to be stationary, and the directional loading mechanism in the fourth through-hole 10 to operate, the stress loading experiment of the rectangle-shaped sample 5 in the front and rear directions is controlled. By controlling the directional loading mechanism in the fifth through-hole 11 to be stationary, and the directional loading mechanism in the sixth through-hole 12 to operate, the stress loading experiment in the vertical direction of the rectangle-shaped sample 5 is controlled. By controlling the directional loading mechanism in the third through-hole 9 to be stationary, and loading the rectangle-shaped sample 5 in different directions by the variable angle loading mechanism, so as to realize the experiment of the rectangle-shaped sample 5 under the condition that the magnitude and direction of the stress are constantly changing. A loading angle of variable angle loading mechanism is ±10°, and can also be made up to ±20° according to requirements.

Further, in order to ensure that the variable angle loading mechanism can apply different magnitudes of stress to the rectangle-shaped sample 5, a first pressure cylinder 13 is arranged between the two arc-shaped tension beams 6, an output end of the first pressure cylinder 13 is fixedly connected to a pressure pad 14, a side of the pressure pad 14 away from the first pressure cylinder 13 is fixedly connected to a side of the load sensor 15, another side of the load sensor 15 is fixedly connected to a round indenter 16, and the round indenter 16 is configured to abut against the rectangle-shaped sample 5. An output compressive stress is provided and controlled by the first pressure cylinder 13, and the magnitude of the compressive stress is monitored by the load sensor 15 to thereby avoid output stress being too large or too small. The rectangle-shaped sample 5 is directly squeezed by the round indenter 16 on the first pressure plate 18 to provide the compressive stress for the rectangle-shaped sample 5 and control the magnitude of the compressive stress. In order to ensure that the variable angle loading mechanism can apply stresses with different angles to the rectangle-shaped sample 5, piston cylinders 17 are symmetrically hinged on the first pressure cylinder 13, each of the piston cylinders 17 is located between the two arc-shaped tension beams 6 and is rotatably connected to the two arc-shaped tension beams 6. By controlling one of the piston cylinders 17 to extend and the other piston cylinder 17 to retract, the first pressure cylinder 13 is controlled to move along the shape of the arc-shaped tension beam 6 between the two arc-shaped tension beams 6, so as to provide stress in different directions for the rectangle-shaped sample 5.

Further, in order to ensure that the rectangle-shaped sample 5 is uniformly subjected to compressive stresses by the variable angle loading mechanism and the directional loading mechanisms, an outside of the rectangle-shaped sample 5 is fixedly connected to a first pressure plate 18 and multiple second pressure plates 19, the variable angle loading mechanism abuts against the first pressure plate, and each of the directional loading mechanisms abuts against each of the second pressure plates 19. The variable angle loading mechanism and the directional loading mechanisms apply stresses to the first pressure plate 18 and the second pressure plates 19 respectively, and squeeze the rectangle-shaped sample 5 by pushing the first pressure plate 18 and the second pressure plates 19 to ensure that each surface of the rectangle-shaped sample 5 is uniformly stressed. Moreover, in order to ensure that when the first pressure cylinder 13 moves between the two arc-shaped tension beams to change the stress angle, the round indenter 16 slides on the first pressure plate 18, a side of the first pressure plate 18 away from the rectangle-shaped sample 5 is provided with an arc-shaped groove 20 matched with the round indenter 16, and the round indenter 16 abuts against the arc-shaped groove 20. The round indenter 16 is limited by the arc-shaped groove 20, and the friction between the round indenter 16 and the first pressure plate 18 is reduced.

Further, in order to ensure that the first pressure cylinder 13 slides between the two arc-shaped tension beams and limit the position of the first pressure cylinder 13 at the same time, so as to prevent the first pressure cylinder 13 from popping out in the opposite direction of the rectangle-shaped sample 5, a side of the first pressure cylinder 13 is fixedly connected to two pulling plates 21, the two pulling plates 21 are both located on the sides of the two arc-shaped tension beams 6 away from the bottom plate 1, an end of each of the two pulling plates 21 is rotatably connected with a roller 22, and the roller 22 is slidably engaged with the arc-shaped tension beam 6. A side of the first pressure cylinder 13 away from the pulling plates 21 is fixedly connected to the supporting plates 23, the supporting plates 23 are located on a side of the arc-shaped tension beam 6 close to the base 2, an end of each of supporting plates 23 is fixedly connected to another roller 22, the roller 22 is slidably engaged with the arc-shaped tension beam 6, and the rollers 22 are all located on a side of the top arc-shaped tension beam 6 away from the bottom plate 1. In order to ensure that the pulling plates 21 can limit the first pressure cylinder 13 and provide installation positions for the rollers 22, a length of the pulling plate 21 is greater than the sum of a thickness of twice one arc-shaped tension beam and a distance between the two arc-shaped tension beams, and less than the sum of the thickness of three times one arc-shaped tension beam and the distance between the two arc-shaped tension beams. A length of the supporting plate 23 is less than the thickness of twice one arc-shaped tension beam. The rollers 22 on the supporting plates 23 and the rollers 22 on the pulling plates 21 ensure that the first pressure cylinder 13 slides between the two arc-shaped tension beams. At the same time, the supporting plates 23 and the pulling plates 21 are configured to limit the first pressure cylinder 13 to ensure that the first pressure cylinder 13 is always between the two arc-shaped tension beams.

Further, in order to provide opposite support force for the variable angle loading mechanism and ensure that when the variable angle loading mechanism applies stress, opposite face of the rectangle-shaped sample 5 is in a stationary state, a side of the bottom plate 1 away from the arc-shaped tension beam 6 is fixedly connected to columns 25, an end of each of the columns 25 away from the bottom plate 1 is fixedly connected to a lower beam 3, a top surface of the bottom plate 1 is fixedly connected to supporting pillars 26, an end of each of the supporting pillars 26 away from the floor is fixedly connected to the lower beam 3, and the lower beam 3 is provided with a mounting hole. The directional loading mechanism in the third through-hole 9 may include a second pressure cylinder 27 fixedly connected in the mounting hole, a piston end of the second pressure cylinder 27 extends into the rock-sample accommodating cavity 4 through the third through-hole 9 and is fixedly connected to a side of another pressure pad 14 (i.e., a second pressure pad), the other side of the pressure pad 14 is fixedly connected to a side of another load sensor 15 (i.e., a second load sensor), the other side of the load sensor 15 is fixedly connected to a ball seat 29, the ball seat 29 is rotatably connected to a joint 28, and the joint 28 abuts against the second pressure plate 19. The second pressure cylinder 27 applies an extrusion stress opposite to the variable angle loading mechanism to the rectangle-shaped sample 5, so as to ensure that the opposite surface of the rectangle-shaped sample 5 is in a stationary state when the rectangle-shaped sample 5 is squeezed by the stress of the variable angle loading mechanism.

Further, in order to monitor an extension length of a piston end of the first pressure cylinder 13 and an extension length of a piston end of the second pressure cylinder 27, each of the first pressure cylinder 13 and the second pressure cylinder 27 is mounted a displacement sensor 30 thereon.

Further, in order to apply compressive stress to the front of the rectangle-shaped sample 5 and ensure that its opposite rear is in a fixed state, directional loading mechanisms are arranged in the second through-hole 8 and the fourth through-hole 10. In order to apply compressive stress to a vertical direction of the rectangle-shaped sample 5 and ensure that its opposite bottom surface is in a fixed state, directional loading mechanisms are arranged in the fifth through-hole 11 and the sixth through-hole 12. The directional loading mechanism in the second through-hole 8 is driven to apply compressive stress to the rectangle-shaped sample 5, while the directional loading mechanism in the fourth through-hole 10 remains stationary to realize the experiment of applying the stress to the sample in the front and rear directions. By driving the directional loading mechanism in the fifth through-hole 11 to apply compressive stress to the sample, while the directional loading mechanism in the sixth through-hole 12 remains stationary, a stress loading experiment on the rectangle-shaped sample 5 in the vertical direction is realized. A directional stress loading part may include second pressure cylinders 27 fixedly connected in the second through-hole 8, the fourth through-hole 10, the fifth through-hole 11 and the sixth through-hole 12 respectively. The piston end of each of the second pressure cylinders 27 is fixedly connected to the pressure pad 14, a side of the pressure pad 14 away from the first pressure cylinder 13 is fixedly connected to a side of the load sensor 15, the other side of the load sensor 15 is fixedly connected to a side of the ball seat 29, the other side of the ball seat 29 is fixedly connected to a joint 28, and the joint 28 is arranged adjacent to the second pressure plate 19.

Further, in order to ensure that the piston cylinder 17 can adjust the angle in time when the first pressure cylinder 13 rotates between the two arc-shaped tension beams, rotating sleeves 31 are arranged between the two arc-shaped tension beams 6, the rotating sleeves 31 are rotatably connected to the two arc-shaped tension beams 6, and the piston cylinders 17 are located between the rotating sleeves 31 and rotatably connected to the rotating sleeves 31 respectively.

Further, in order to ensure that the piston cylinders 17 can be hinged on both sides of the first pressure cylinder 13, both sides of the first pressure cylinder 13 are fixedly connected to articulated bases 32 respectively, and output ends of two piston cylinders 17 are hinged on the articulated bases 32 respectively.

When the disclosure is used, five surfaces of the prepared rectangle-shaped sample 5 are fixedly connected to the second pressure plates 19 respectively, and the remaining one surface is fixed to the first pressure plate 18. The rectangle-shaped sample 5 is placed into the rock-sample accommodating cavity 4, the first pressure plate 18 abuts against the round indenter 16 of a variable angle loading part, and the directional loading mechanism in the fourth through-hole 10, the sixth through-hole 12 and the third through-hole 9 is in a stationary state. Then, the second pressure cylinders 27 in the second through-hole 8 and the fifth through-hole 11, and the pressure cylinder are started to drive the joint 28 on the ball seat 29 to thereby generate a compressive stress on the rectangle-shaped sample 5 in the front and rear vertical direction, so as to perform an experiment the rectangle-shaped sample 5. At the same time, the second pressure cylinder 27 can be used to control the magnitude of the compressive stress to carry out experiments on the rectangle-shaped sample 5 under the condition of different magnitudes of compressive stress. The first pressure cylinder 13 between the two arc-shaped tension beams is started to drive the round indenter 16 to thereby provide compressive stress to the rectangle-shaped sample 5. At the same time, the piston cylinders 17 are started to drive the first pressure cylinder 13 to thereby rotate between the two arc-shaped tension beams through the piston cylinders 17, so as to simulate the stress of the rectangle-shaped sample 5 in different magnitudes and directions.

The disclosure discloses a multi-directional loading testing device, which can simulate loading and unloading of a stress with changing direction and magnitude under excavation disturbance, and is of great significance for understanding the mechanical behavior of rock-soil mass under excavation disturbance.

In the description of the disclosure, it should be understood that the orientations or positional relationships indicated by the terms "longitudinal", "transversal", "upper", "lower", "front", "rear", "left", "right", "vertical", "horizontal", "top", "bottom", "inner" and "outer" are based on the orientations or positional relationships shown in the accompanying drawings, and are only for the convenience of describing the disclosure, rather than indicating or implying that a device or element must have a specific orientation, be configured/constructed and operated in a specific orientation, and therefore cannot be understood as a limitation of the disclosure.

The above embodiments only describe preferred embodiments of the disclosure and do not limit the scope of the disclosure. Without departing from the design spirit of the disclosure, various modifications and changes made by those of ordinary skill in the art to the technical solution of the disclosure should fall within the protection scope determined by the appended claims of the disclosure.

What is claimed is:

1. A variable angle loading testing machine, comprising: a bottom plate and a base fixedly connected to the bottom plate;
   wherein a rock-sample accommodating cavity is formed in the base, and the rock-sample accommodating cavity is configured to be placed a rectangle-shaped sample therein;
   wherein a side of the base is fixedly connected to two arc-shaped tension beams arranged in parallel, a variable angle loading mechanism is slidably connected between the two arc-shaped tension beams; and
   wherein through-holes are formed on the base, and an output end of the variable angle loading mechanism is configured to abut against the rectangle-shaped sample through one of the through-holes.

2. The variable angle loading testing machine according to claim 1, wherein the variable angle loading mechanism comprises a first pressure cylinder slidably connected between the two arc-shaped tension beams, and an output end of the first pressure cylinder is fixedly connected with a pressure pad;
   wherein a side of the pressure pad away from the first pressure cylinder is fixedly connected to a side of a load sensor, another side of the load sensor is fixedly connected to a round indenter, and the round indenter is configured to abut against the rectangle-shaped sample; and
   wherein piston cylinders are symmetrically hinged on the first pressure cylinder, each of the piston cylinders is located between the two arc-shaped tension beams, and each of the piston cylinders is hinged to the two arc-shaped tension beams.

3. The variable angle loading testing machine according to claim 2, wherein a first pressure plate and a plurality of second pressure plates are configured to be fixedly connected to an outside of the rectangle-shaped sample, and the plurality of second pressure plates abut against the rock-sample accommodating cavity, a side of the first pressure plate away from the rectangle-shaped sample is provided with an arc-shaped groove matched with the round indenter, and the round indenter abuts against the arc-shaped groove.

4. The variable angle loading testing machine according to claim 3, wherein a side of the first pressure cylinder away from the pressure pad is fixedly connected to two pulling plates, a side of the first pressure cylinder close to the pressure pad is fixedly connected to supporting plates, and the two arc-shaped tension beams are located between the supporting plates and the two pulling plates; and wherein ends of the two pulling plate and the supporting plates are rotatably connected with rollers, and the rollers are slidably engaged with the arc-shaped tension beam.

5. The variable angle loading testing machine according to claim 3, wherein rotating sleeves are arranged between the two arc-shaped tension beams, the rotating sleeves are rotatably connected to the two arc-shaped tension beams, and the piston cylinders are rotatably connected to the two arc-shaped tension beams through the rotating sleeves respectively.

6. The variable angle loading testing machine according to claim 3, wherein both sides of the first pressure cylinder are fixedly connected to articulated bases respectively, and output ends of the piston cylinders are hinged with the first pressure cylinder through the articulated bases respectively.

7. The variable angle loading testing machine according to claim 4, wherein the through-holes comprise: a first through-hole, a second through-hole, a fourth through-hole, a fifth through-hole and a sixth through-hole;

wherein the second through-hole, the fourth through-hole, the fifth through-hole and the sixth through-hole are located in a same plane; and axes of the second through-hole, the fourth through-hole, the fifth through-hole and the sixth through-hole are all perpendicular to an axis of the first through-hole;

wherein directional loading mechanisms are respectively arranged in the second through-hole, the fourth through-hole, the fifth through-hole and the sixth through-hole; and the directional loading mechanism arranged in the sixth through-hole is fixedly connected to the bottom plate;

wherein output ends of the directional loading mechanisms abut against the second pressure plates; and wherein the variable angle loading mechanism abuts against the first pressure plate through the first through-hole.

8. The variable angle loading testing machine according to claim 7, wherein each of the directional loading mechanisms comprises a second pressure cylinder, a piston end of the second pressure cylinder is fixedly connected to a second pressure pad; and wherein a side of the second pressure pad away from the second pressure cylinder is fixedly connected to a side of a second load sensor, another side of the second load sensor is fixedly connected to a ball seat, an end of the ball seat away from the second load sensor is fixedly connected to a joint, and the joint abuts against the second pressure plate.

9. The variable angle loading testing machine according to claim 8, wherein a third through-hole is formed on a side of the base away from the first through-hole, the third through-hole is coaxial with the first through-hole, and the third through-hole is communicated with the rock-sample accommodating cavity;

wherein the bottom plate is fixedly connected to supporting pillars, an end of each of the supporting pillars away from the bottom plate is fixedly connected to a lower beam, a side of the base away from the arc-shaped tension beams is fixedly connected to columns, and an end of each of the columns away from the base is fixedly connected to the lower beam; and wherein the lower beam is provided with a mounting hole, a directional loading mechanism is installed in the mounting hole and an output end thereof abuts against the second pressure plate through the third through-hole.

10. The variable angle loading testing machine according to claim 8, wherein each of the first pressure cylinder and the second pressure cylinders is mounted a displacement sensor thereon.

* * * * *